(12) United States Patent
Soars (10) Patent No.: US 11,389,591 B2
(45) Date of Patent: Jul. 19, 2022

(54) MARKING AND INJECTION REMOTE DELIVERY DEVICE

(71) Applicant: PNEU-DART, INC., Williamsport, PA (US)

(72) Inventor: Blair D. Soars, Williamsport, PA (US)

(73) Assignee: Pneu-Dart, Inc., Williamsport, PA (US)

( * ) Notice: Subject to any disclaimer, the term of this patent is extended or adjusted under 35 U.S.C. 154(b) by 215 days.

(21) Appl. No.: 16/873,708

(22) Filed: Jun. 8, 2020

(65) Prior Publication Data

US 2021/0379283 A1     Dec. 9, 2021

(51) Int. Cl.
| | |
|---|---|
| *A61M 5/20* | (2006.01) |
| *A61M 5/315* | (2006.01) |
| *G16H 40/67* | (2018.01) |
| *G16H 20/17* | (2018.01) |
| *A61M 5/178* | (2006.01) |
| *A61M 5/19* | (2006.01) |
| *A61M 5/14* | (2006.01) |
| *A01K 11/00* | (2006.01) |
| *A61D 1/02* | (2006.01) |

(52) U.S. Cl.
CPC ...... *A61M 5/2046* (2013.01); *A61M 5/31501* (2013.01); *A61M 5/31511* (2013.01); *G16H 20/17* (2018.01); *G16H 40/67* (2018.01); *A01K 11/00* (2013.01); *A01K 11/007* (2013.01); *A61D 1/025* (2013.01); *A61M 5/1407* (2013.01); *A61M 5/19* (2013.01); *A61M 2005/1787* (2013.01)

(58) Field of Classification Search
CPC ............ A61M 2005/1787; A61M 5/19; A61M 5/1407; A01K 11/00; A01K 11/007; A61D 1/025
See application file for complete search history.

(56) References Cited

U.S. PATENT DOCUMENTS

| | | |
|---|---|---|
| 1,815,300 A | 7/1931 | Harris |
| 2,854,925 A | 10/1958 | Crockford et al. |
| 2,923,243 A | 2/1960 | Crockford et al. |
| 3,022,785 A | 2/1962 | Crockford et al. |
| 3,207,157 A | 9/1965 | Murdock |

(Continued)

*Primary Examiner* — Nathan R Price
*Assistant Examiner* — Tania Ismail
(74) *Attorney, Agent, or Firm* — Thomas R. Shaffer, Esq.

(57) ABSTRACT

A remote delivery device is provided which has media portholes in a sidewall, a tail piece attached to a rear end and a cannula attached to a front end. The body contains a plunger assembly which defines an injectable liquid chamber and a marking media chamber. The plunger assembly includes a front barbell plunger, rear barbell plunger and a plunger shaft with an O-Ring seated between the front and rear of said plunger shaft. The body also contains a single internal charge positioned behind the plunger assembly. When the charge is activated, the plunger assembly is thrust forwardly and dispenses an injectable liquid from the injectable liquid chamber through the cannula. Simultaneously, the plunger assembly also dispenses a marking media from the marking media chamber through marking media portholes. The provision of a single internal charge allows for a reduction in the length and weight of the device. The single internal charge provides evidence of successful injection of the injectable liquid when the media is displaced from the marking media chamber.

9 Claims, 6 Drawing Sheets

(56) References Cited

U.S. PATENT DOCUMENTS

| | | |
|---|---|---|
| 3,209,695 A | 10/1965 | Crockford et al. |
| 3,266,806 A | 8/1966 | Warren et al. |
| 3,457,921 A | 7/1969 | Waldeisen |
| 3,525,319 A | 8/1970 | Waldeisen |
| 4,684,366 A | 8/1987 | Denny et al. |
| 6,482,157 B2 | 11/2002 | Robinson |
| 10,935,355 B2 * | 3/2021 | Brydges-Price ...... F42B 12/367 |
| 2015/0352285 A1 * | 12/2015 | Soars .................. A61M 5/2053 604/130 |
| 2018/0250110 A1 * | 9/2018 | Miller ................. A61M 5/2053 |

* cited by examiner

MARKING AND INJECTION REMOTE DELIVERY DEVICE

BACKGROUND OF THE INVENTION

1. Field of the Invention

The present invention relates to a remote delivery device. More specifically, the present invention relates to a remote delivery device which provides both a marking function and an injection function with the use of a single charge or ignition system.

2. Description of the Prior Art

The provision of remote delivery devices which provide for both the injection of a liquid into an animal as well as a marking function wherein the sight of the injunction is sprayed with a marking media is well known. The use for such marking and injection devices are also well known. The structure and operation of a typical prior art marking and injection remote delivery device is that a body is provided which contains two compartments each containing a plunger and an ignition system. The forward compartment is the injectable liquid chamber and the rear compartment is allocated to the marking media chamber. Upon impact each independent ignition system within the device activates and forces each plunger within each body compartment to inject the drug along with applying an external mark on the animal.

The structure of a known prior art marking and injection device can be seen with the provision of a mid-span crimp which separates the forward injectable liquid chamber of the device from the rear marking media chamber and holds the internal charge. Behind the crimp there are typically a number of marking media ejection ports.

While existing marking and injection remote delivery devices are useful, they tend to be overly long in length which reduces the accuracy of the projectile and tend to be overly heavy which can cause injury to the animal.

SUMMARY OF THE INVENTION

While the concept of providing a simultaneous injection of injectable liquid along with dispensing marking media to the external surface of an animal is not new, the internal components, specifically the provision of a unique plunger assembly of the present invention reduces the need for two internal charges thereby reducing the net weight and length of the remote delivery device itself. The reduction in length improves accuracy and the reduction in weight reduces the potential for induced hematomas at the point of impact. Hematomas (coagulated blood) can cause prolonged induction time of the intended sedative and can often cause "secondary sedation" whereby the animal succumbs to residual amounts of the drug leaching into the vascular network long after conventional metabolization intervals had transpired which when prevalent can expose the animal to physical harm including, but not limited to, predation.

In its simplest form, the present invention provides a remote delivery device comprising a body having at least one marking media porthole in a sidewall thereof and a cannula attached to a front end of said body, said body containing a plunger assembly defining an injectable liquid chamber and a marking media chamber, said body containing a single internal charge positioned rearward of said plunger assembly whereby when said single internal charge is activated, said plunger assembly is thrust forwardly dispensing an injectable liquid from said injectable liquid chamber through said cannula and dispensing a marking media from said marking media chamber through said at least one marking media porthole.

Preferably the remote delivery device further comprising a tail piece crimped onto a rear end of said body.

Preferably the plunger assembly further comprises a front barbell plunger, rear barbell plunger and a plunger shaft.

Preferably the plunger shaft further comprises a front shaft portion with small circular flanges at each end of said front portion, large circular flanges at each end of said rear portion and a O-ring seated between said front shaft portion and said rear shaft portion.

Preferably the single internal charge further comprises a firing pin, a spring and an ignition system and plug.

Preferably when said single internal charge is activated, a controlled explosion occurs within said body creating pressure which moves said plunger assembly from an initial position to a final discharged position.

Preferably the single internal charge is activated when the remote delivery device strikes a target and the remote delivery device is rapidly slowed or stopped.

The provision of a single internal charge allows the remote delivery device to have less weight and a shorter length than a remote delivery device which requires two separate charges, one for the dispensing of an injectable liquid and another for the dispensing of a marking media whereby increasing accuracy and reducing the potential for an induced hematoma at the point of impact. The single internal charge provides evidence of successful injection of the injectable liquid when the marking media is displaced from the marking media chamber.

Preferably the remote delivery device includes a flow restrictor to reduce the rate of flow of an injectable liquid through said cannula.

DETAILED DESCRIPTION OF THE PREFERRED EMBODIMENTS

Figure 1:
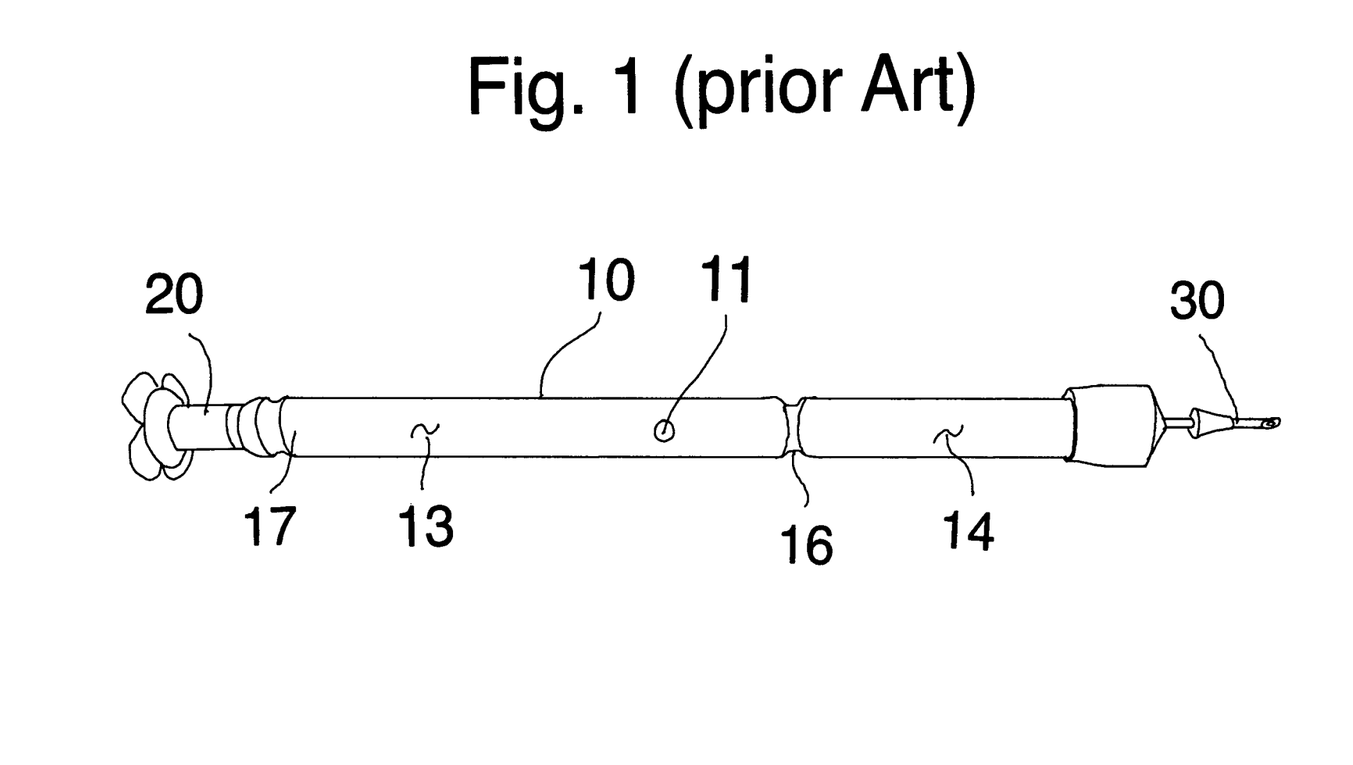
FIG. 1 is a side elevational view of a prior art remote delivery device which provides both a marking and injection function.

Referring to FIG. 1, a prior art remote delivery device which provides both a marking and injection function is shown. The device includes a body 10, at least one marking media port hole 11, a cannula 30 located on a front end thereof, a tailpiece 20 crimped onto a rear end of the body 10, and, as shown the body includes two chambers, namely a forward injectable liquid chamber 14 and a rearward marking media chamber 13. Explosive charges including a plunger are provided at both locations 16 and 17. The forward explosive charge and plunger are provided at the location of the crimped body as shown at location 16.

Figure 2:
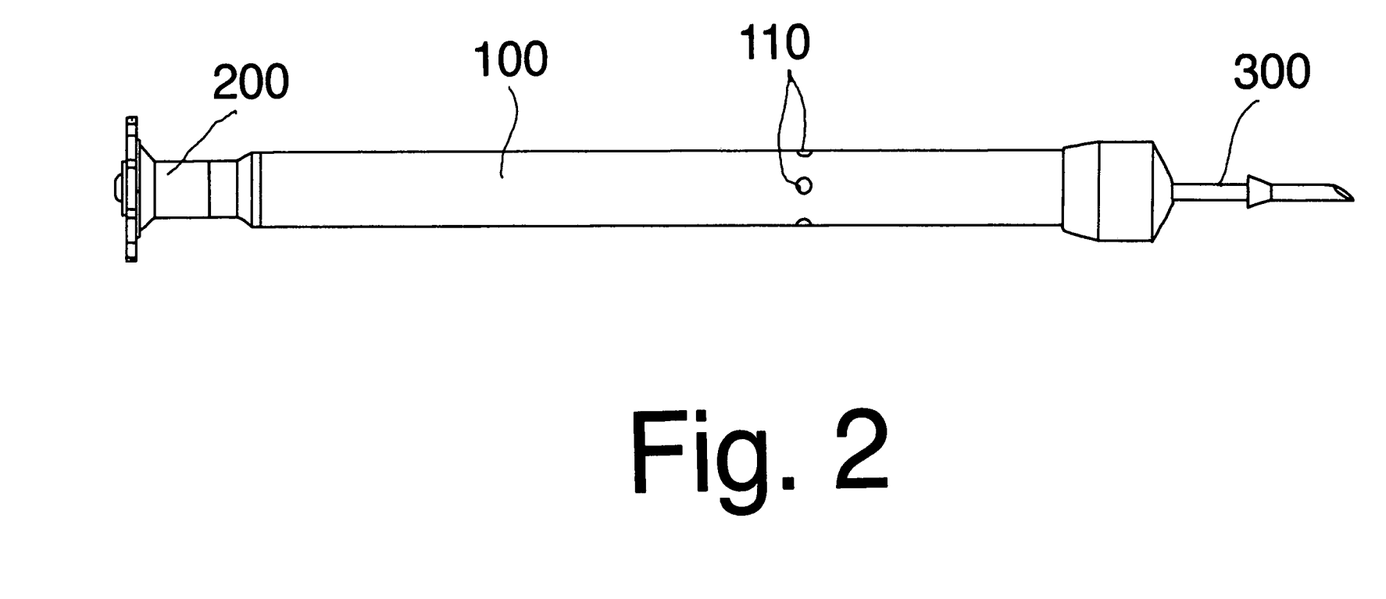
FIG. 2 is a side elevational view of the present invention.

Referring to FIG. 2, the present invention provides a remote delivery device which includes a body 100, a plurality of marking media portholes 110 provided in a side wall of said body 100, a cannula 300 attached by means of a ferrule 310 at a forward end of said body 100 and a tailpiece 200 which is attached to a rear end of body 100.

Figure 3:
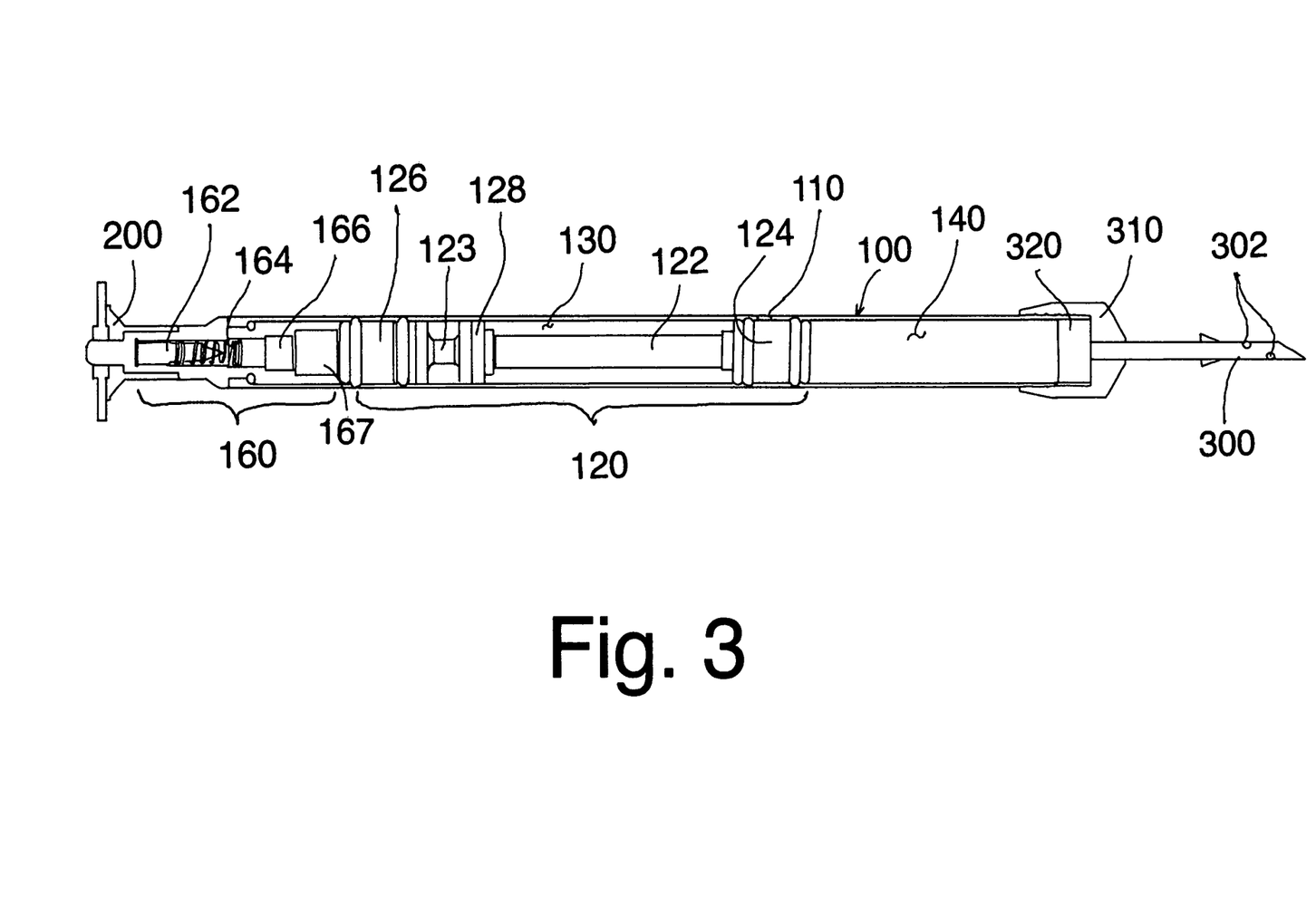
FIG. 3 is a cross sectional view of the present invention in an initial ready condition.

With reference to FIG. 3, the internal components of the remote delivery device of the present invention are shown in an initial ready position. The device includes a body 100 with a cannula 300 attached at a forward end thereof by means of a ferrule 310. The cannula 300 has a number of cannula portholes 302 provided to allow the discharge of an injectable liquid through the hollow cannula 300. Just rearward of the cannula 300 a flow restrictor 320 is provided. This restrictor reduces the rate of flow of an injectable liquid that can reach the cannula upon discharge of the device.

A unique feature of the present invention is the provision of the plunger assembly 120. The plunger assembly 120 includes a plunger shaft 122, a front barbell plunger 124 a rear barbell plunger 126 and O-ring 128. The plunger shaft 122 includes a long forward section which includes a small circular flange on each end thereof and a rear section 123 which includes a large circular flange on each end thereof. The plunger shaft 122 and 123 is formed from a single piece of machined material and includes a groove or location seat for the provision of the O-ring 128.

As shown, the front barbell plunger 124 seals off and prevents liquid from flowing through a marking media porthole 110 which is provided in a side wall of the body 100. Preferably, five (5) such marking media portholes 110 are provided around the circumference of said body with said barbell plunger 124 providing a seal for all such marking media portholes in the initial condition. The device also includes a single internal charge 160 which includes a firing pin 162, a spring 164 and an ignition system 166 and plug 167. The single internal charge 160 is activated upon impact with an animal.

A tailpiece 200 is provided at the rear end of body 100.

Figure 4:
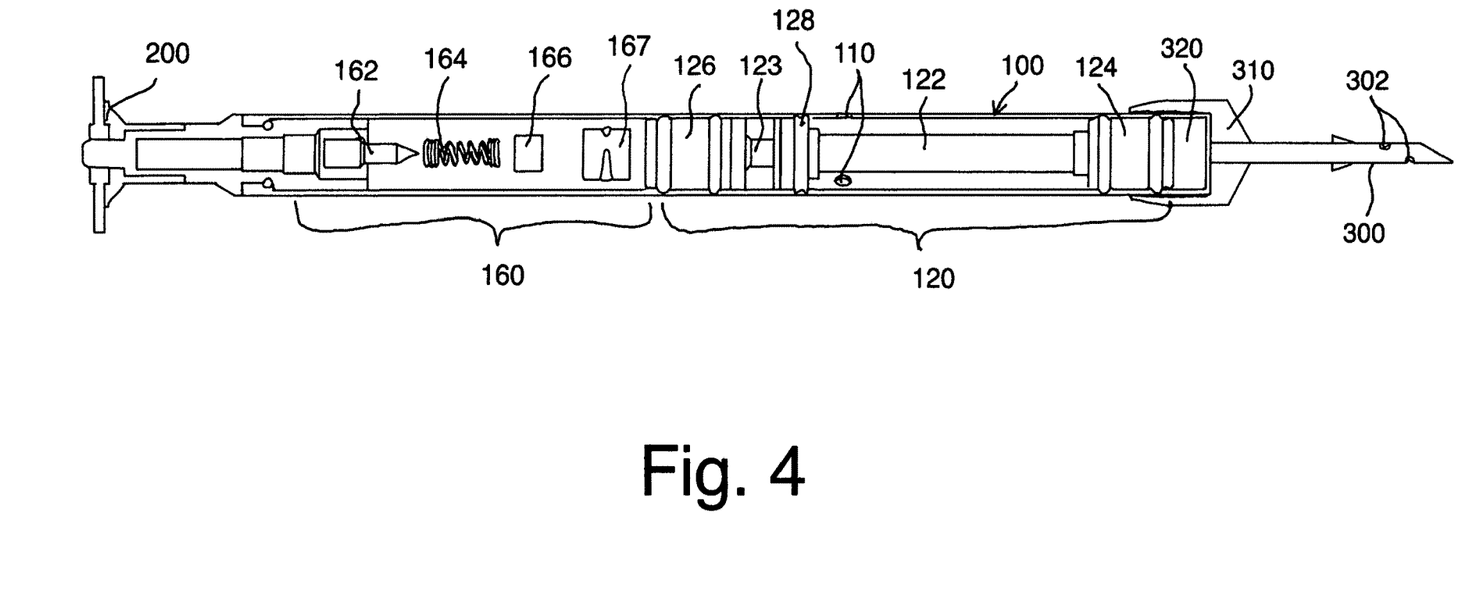
FIG. 4 is a cross sectional view of the present invention in a final discharged condition.

Referring now to FIG. 4 the internal components of the remote delivery device of the present invention can be shown in a final discharged position. All of the reference numbers remain the same as in FIG. 3. As can be seen, upon the activation of the single internal charge 160 the ignition system explodes causing pressure which urges or forces the entire plunger assembly 120 forwardly toward the cannula 300. During this operation, when the plunger assembly 120 is moving forward, the injectable liquid is dispensed through the cannula and the marking media from the marking media chamber is discharged through the marking media portholes 110.

Figure 5:
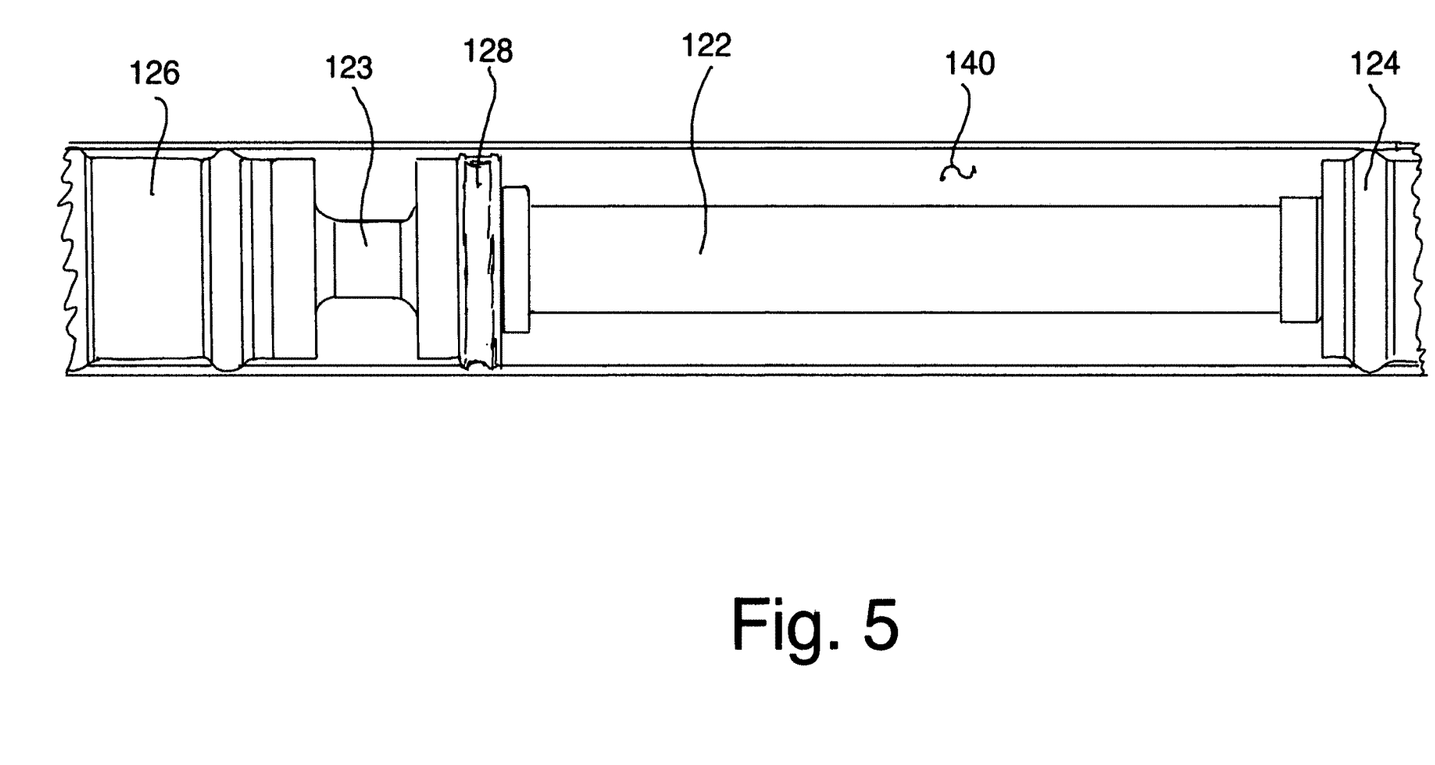
FIG. 5 is an enlarged cross-sectional view showing the plunger assembly of the present invention.

Referring to FIG. 5, an enlarged view of the various components of the plunger assembly 120 are shown in greater detail as described above.

Figure 6:
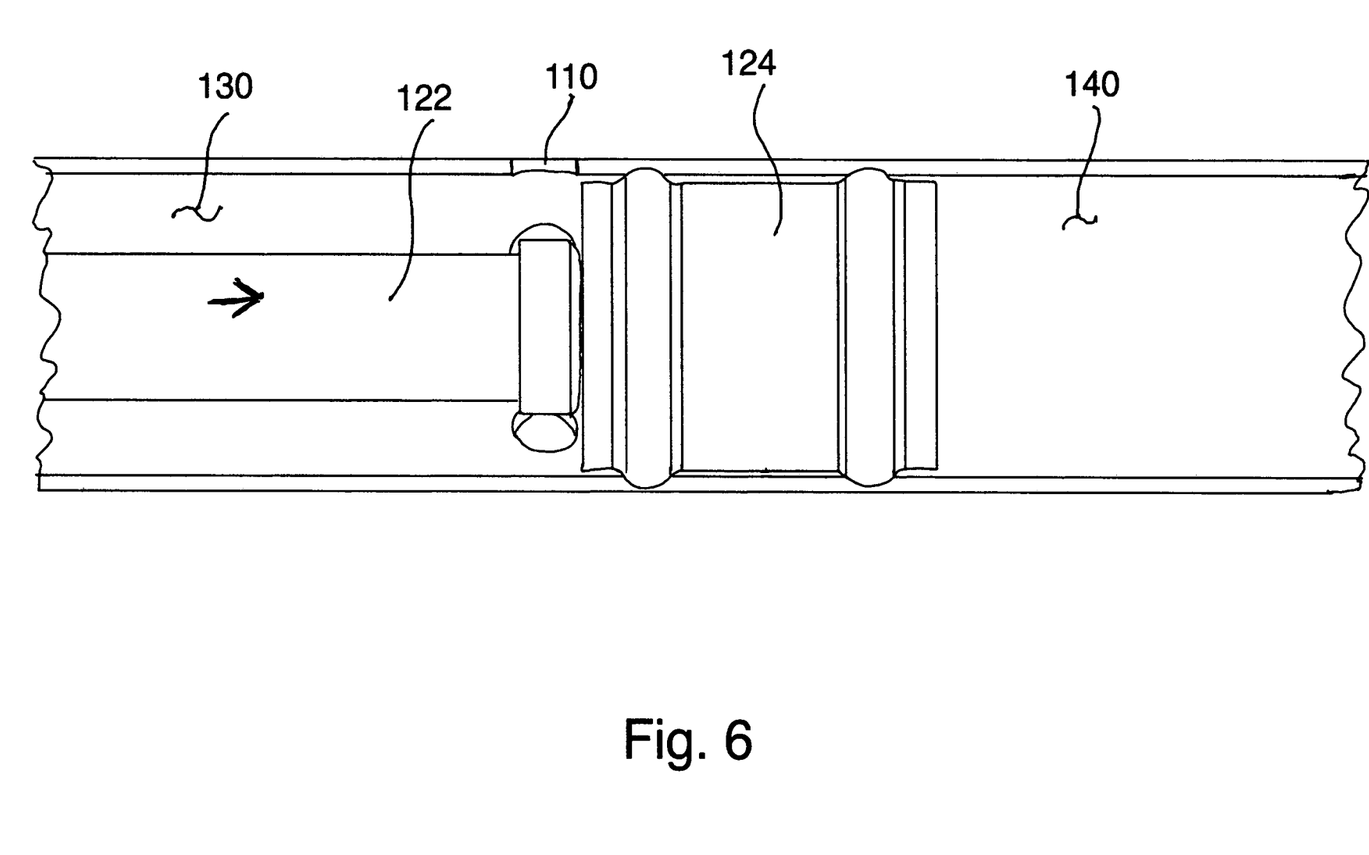
FIG. 6 is an enlarged cross-sectional view showing that forward motion of the front barbell plunger exposes the marking media port hole allowing discharge of a marking media.

Referring to FIG. 6, an enlarged view showing the location of the injectable liquid chamber 140 and marking media chamber 130 immediately after the discharge of the single internal charge which moves the entire plunger assembly forward in the direction of the arrow shown on plunger shaft 122. As shown, as the front barbell plunger 124 moves forwardly the marking media from the marking media chamber is forced from the marking media portholes 110 which are now no longer sealed by the front barbell plunger 124.

With this arrangement, only a single internal charge 160 is needed to provide for the dispensing of both an injectable liquid from injectable liquid chamber 140 and a marking media from marking media chamber 130. It will be understood that when the single internal charge is activated, a controlled explosion occurs within the body 100 creating pressure which moves the plunger assembly 120 from an initial position as shown in FIG. 3 to a final discharged position as shown in FIG. 4.

Because the present invention utilizes only a single internal charge this allows the remote delivery device to have less weight and to be shorter than a prior art remote delivery device which requires two separate charges, one for the dispensing of an injectable liquid and another for the dispensing of a marking media. This allowing for a reduction in the length of the remote delivery remote delivery device increases the accuracy. The reduction in weight of the remote delivery device reduces the potential for an induced hematoma at the point of impact. Further, the single internal charge provides evidence of successful injection of the injectable liquid when the marking media is displaced from the marking media chamber.

It is to be understood that while certain forms of the present invention have been illustrated and described herein, the present invention is not to be limited to the specific forms or arrangements of parts described and shown.

I claim:

1. A remote delivery device comprising a body having a least one marking media porthole in a sidewall thereof and a cannula attached to a front end of said body, said body containing a plunger assembly defining an injectable liquid chamber and a marking media chamber, said body containing a single internal charge positioned rearward of said plunger assembly whereby when said single internal charge is activated, said plunger assembly is thrust forwardly dispensing an injectable liquid from said injectable liquid chamber through said cannula and dispensing a marking media from said marking media chamber through said at least one marking media porthole.

2. A remote delivery device according to claim 1 further comprising a tail piece crimped onto a rear end of said body.

3. A remote delivery device according to claim 1 wherein said plunger assembly further comprises a front barbell plunger, rear barbell plunger and a plunger shaft with a grooved O-Ring seat.

4. A remote delivery device according to claim 3 wherein said plunger shaft further comprises a front shaft portion with small circular flanges at each end of said front portion, a rear portion with large circular flanges at each end of said rear barbell portion and a O-ring seated between said front plunger shaft portion and said rear plunger shaft portion.

5. A remote delivery device according to claim 1 wherein said single internal charge further comprises a firing pin, a spring and an ignition system and plug.

6. A remote delivery device according to claim 1 wherein when said single internal charge is activated, a controlled explosion occurs within said body creating pressure which moves said plunger assembly from an initial position to a final discharged position.

7. A remote delivery device according to claim 1 wherein said single internal charge is activated when the remote delivery device strikes a target and the remote delivery device is rapidly slowed or stopped.

8. A remote delivery device according to claim 1 wherein the provision of a single internal charge allows the remote delivery device to have less weight and a shorter length than a remote delivery device which requires two separate charges, one for the dispensing of an injectable liquid and another for the dispensing of a marking media whereby increasing accuracy and reducing the potential for an induced hematoma at the point of impact and wherein the single internal charge provides evidence of successful injection of the injectable liquid when the media is displaced from the media chamber.

9. A remote delivery device according to claim 1 further comprising a flow restrictor to reduce the rate of flow of an injectable liquid through said cannula.

* * * * *